(12) United States Patent
Bauer et al.

(10) Patent No.: US 7,067,765 B2
(45) Date of Patent: Jun. 27, 2006

(54) METHODS FOR FORMING ELECTRICALLY ACTIVE SURFACES FOR MEDICAL ELECTRICAL LEADS

(75) Inventors: Ryan T. Bauer, Brooklyn Park, MN (US); Daniel R. Pavlik, Ramsey, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 102 days.

(21) Appl. No.: 10/923,925

(22) Filed: Aug. 23, 2004

(65) Prior Publication Data

US 2006/0037195 A1    Feb. 23, 2006

(51) Int. Cl.
*B23K 26/38* (2006.01)
(52) U.S. Cl. .................................. 219/121.69
(58) Field of Classification Search .......... 219/121.68, 219/121.69, 121.85; 607/116, 119; 29/825, 29/867; 264/400
See application file for complete search history.

(56) References Cited

U.S. PATENT DOCUMENTS

| | | | |
|---|---|---|---|
| 5,935,465 A | 8/1999 | Cardineau et al. | 219/121.69 |
| 6,265,691 B1* | 7/2001 | Cardineau et al. | 219/121.69 |
| 6,355,401 B1* | 3/2002 | Graves et al. | 219/121.69 |
| 6,374,488 B1 | 4/2002 | McLean et al. | 29/867 |
| 6,401,334 B1 | 6/2002 | McLean et al. | 29/860 |
| 6,640,436 B1 | 11/2003 | Kimura et al. | 29/867 |

* cited by examiner

*Primary Examiner*—Geoffrey S. Evans
(74) *Attorney, Agent, or Firm*—Michael C. Soldner; Girma Wolde-Michael

(57) ABSTRACT

A method for forming an electrically active surface for a medical electrical lead includes the steps of inserting a conductor coil into a shroud that includes an opening, lifting an end of at least one filar of a plurality of filars forming the coil out through the opening, and removing a layer of insulation from about the end of the at least one filar by means of laser ablation.

24 Claims, 8 Drawing Sheets

METHODS FOR FORMING ELECTRICALLY ACTIVE SURFACES FOR MEDICAL ELECTRICAL LEADS

TECHNICAL FIELD

The present invention is related to medical electrical leads and more particularly to methods for forming conductive or electrically active surfaces of the leads.

BACKGROUND

Cardiac stimulation systems commonly include a pulse-generating device, such as a pacemaker or implantable cardioverter/defibrillator that is electrically connected to the heart by at least one medical electrical lead. A medical electrical lead delivers electrical pulses emitted by the pulse generator to the heart, stimulating the myocardial tissue via electrodes included on the lead. Cardiac signals may also be sensed by lead electrodes and conducted, via the lead, back to the device to monitor the electrical activity of the heart. These leads are coupled to the devices via connector terminals carrying one or more contact surfaces, which are in turn coupled to corresponding lead electrodes by elongate conductors extending within the lead.

In many instances a coiled wire or wires form lead conductors and, in order to maintain a low profile, a single coiled conductor of a lead may include multiple wire filars forming independent circuits between multiple electrodes and corresponding connector contact surfaces. In order to maintain electrical isolation between the independent filar circuits of a coiled conductor, an insulative layer is formed about one or more of the filars. In order to electrically couple an insulated wire filar to an electrode, and to a corresponding connector contact, portions of the insulative layer are removed to expose an electrically active surface of the conductor.

Although embodiments of the present invention have been introduced in the context of cardiac stimulation systems, it should be understood that the invention is not so limited, being applicable for medical electrical leads applied for any therapeutic and/or diagnostic purpose.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
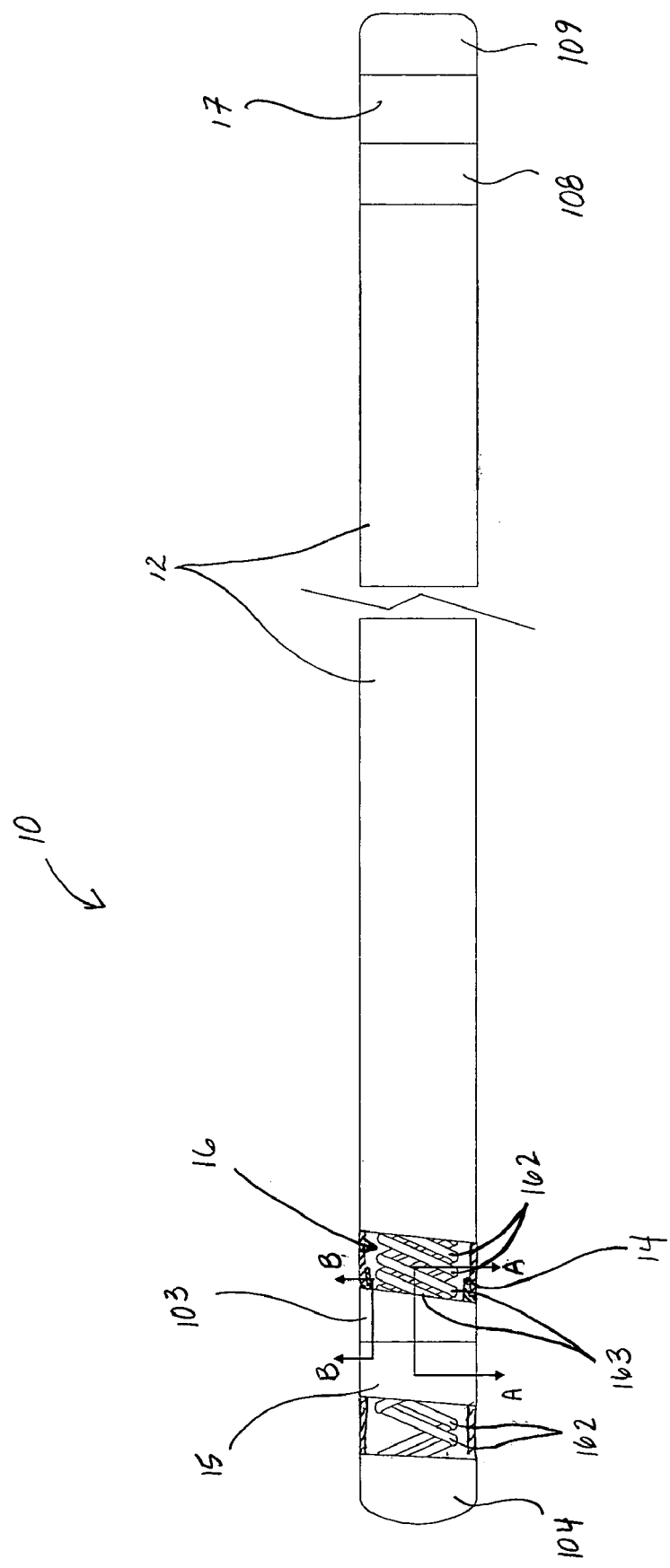
FIG. 1 is a plan view with partial cut-away sections of an exemplary medical electrical lead.

FIG. 1 is a plan view with partial cut-away sections of an exemplary medical electrical lead 10. FIG. 1 illustrates a lead body 12 including an elongate quadra-filar conductor coil 16 extending within an insulative sheath 14; coil 16 includes a first pair of filars 162 electrically coupling a tip electrode 104 to a first connector contact 109 and a second pair of filars 163 coupling a ring electrode 103 to a second connector contact 108. FIG. 1 further illustrates a distal insulative spacer 15 isolating ring electrode 103 from tip electrode 104 and a proximal insulative spacer 17 likewise isolating first connector contact 109 from second connector contact 108. At least each wire of second filar pair 163 includes an insulative layer formed thereover (shown in FIGS. 2B and 3) to isolate pair 163 from first filar pair 162. According to one example, filar pairs 162, 163 are formed from MP35N alloy wire insulated with a fluoropolymer, polyurethane, silicone or polyimide.

As illustrated in FIG. 1, second filar pair 163 is terminated beneath ring electrode 103 for the coupling and, according to methods of the present invention, has had a portion of the insulative layer removed to expose an electrically active surface of underlying wires for the coupling. Likewise, another portion of the insulative layer has been removed from an opposite end of second filar pair 163, which is electrically coupled to second connector contact 108. Means for electrical coupling may include, for example crimping, press-fit and welding; two such means will be further described in conjunction with FIGS. 5A–B.

Figure 2A:
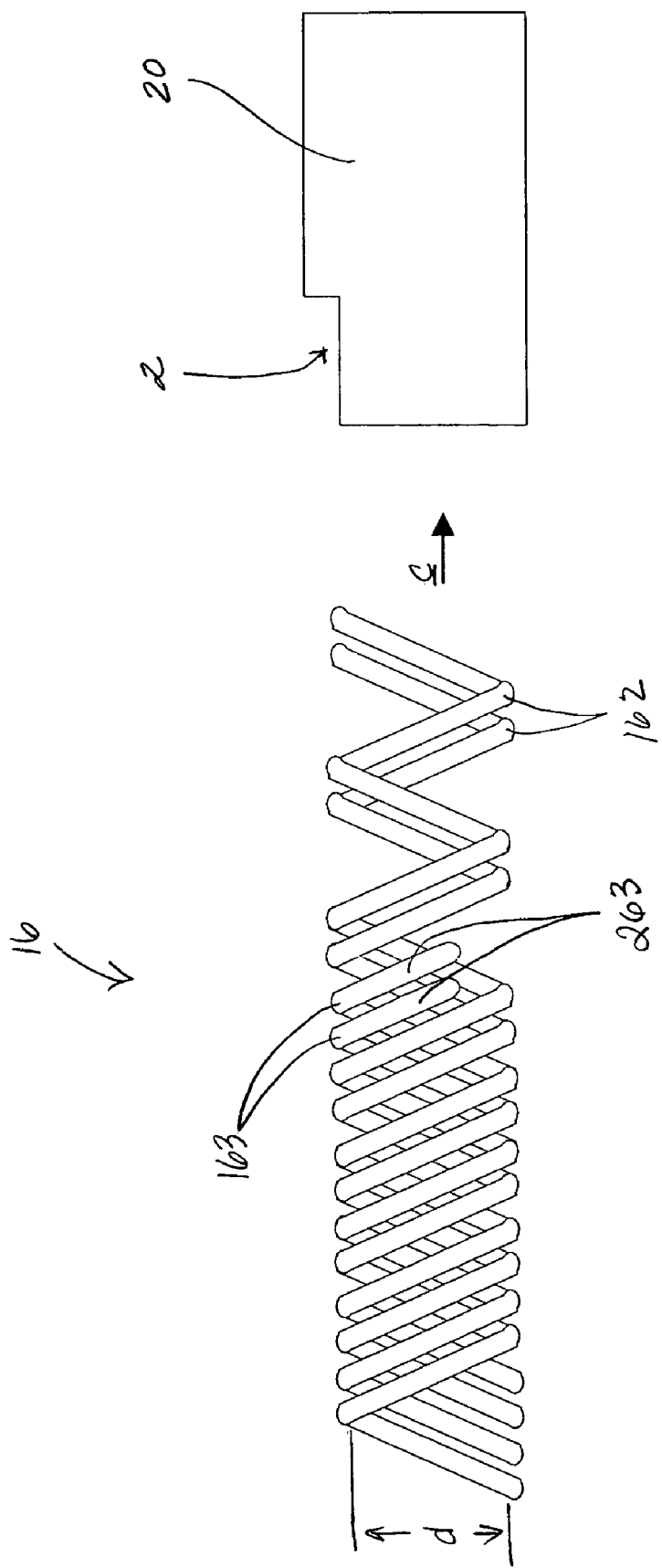
FIG. 2A is a plan view of a conductor coil and a shroud according to an initial step of a method of the present invention.

FIG. 2A is a plan view of conductor coil 16 and a tubular shroud 20 according to an initial step of a method of the present invention. FIG. 2A illustrates coil 16 directed, per arrow C, toward a bore (not shown) of shroud 20. FIG. 2A further illustrates shroud 20 including an opening or a slot 2 out from which ends 263 of filar pair 163 will be lifted when coil is fully inserted within the bore of shroud 20. Shroud 20 can be made of stainless steel.

Figure 2B:
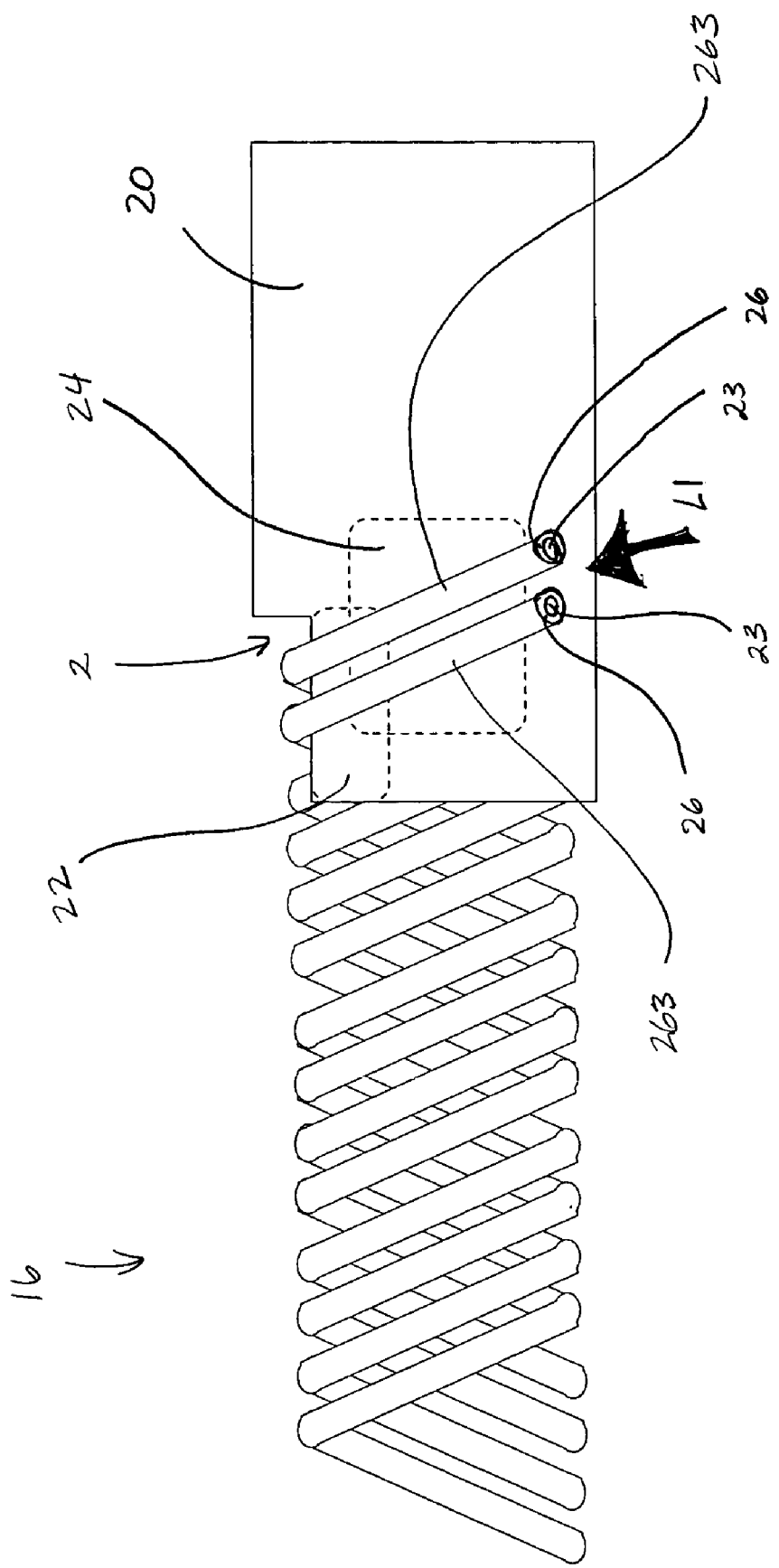
FIG. 2B is a plan view of a conductor coil and a shroud according to another step of a method of the present invention.

FIG. 2B is a plan view of conductor coil 16 fully inserted within shroud 20 showing ends 263 extending out from slot 2 and around an outer surface of shroud 20. According to a method of the present invention, ends 263 of filar pair 163 are thus exposed for removal of a portion of insulative layers 26, for example by laser ablation, while other portions of filar pair 163 and portions of filar pair 162, which are within the bore, are shielded from the removal process.

Figure 2C:
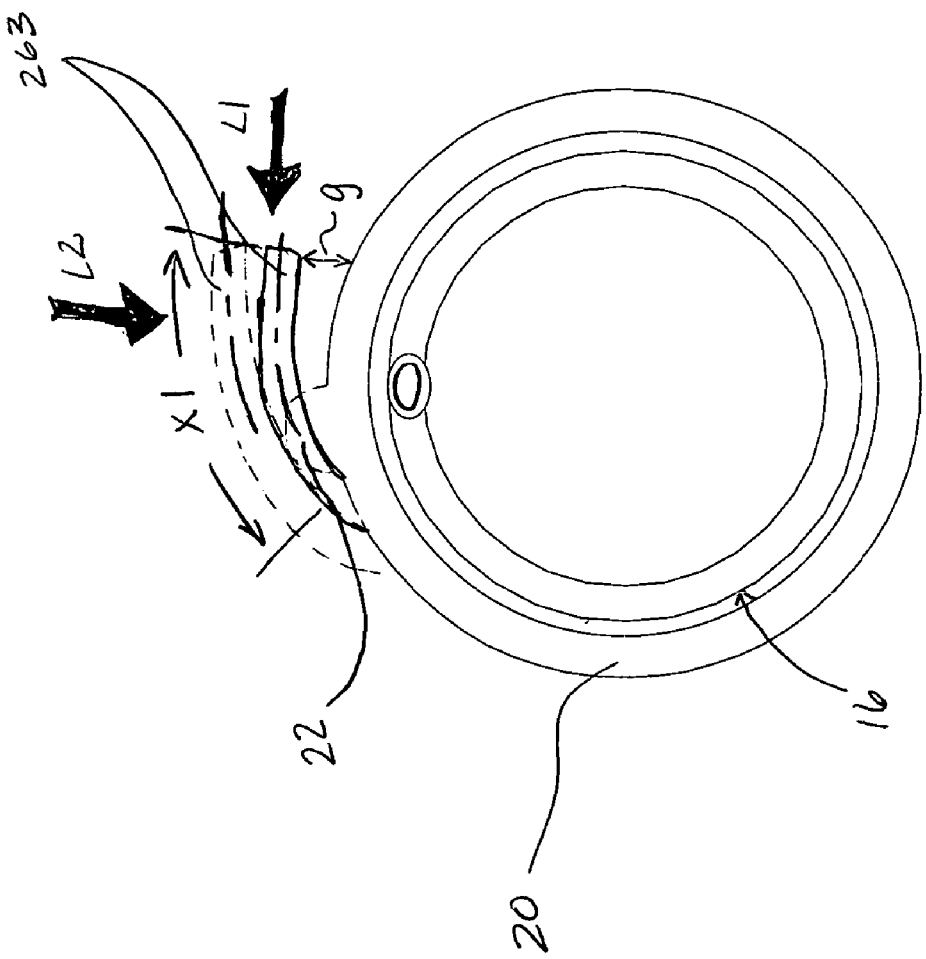
FIG. 2C is an end view of the conductor coil and shroud shown in FIG. 2B.

FIG. 2B further illustrates a general direction of a laser beam L1, which, according to a preferred method, will remove insulation 26 from approximately 360 degrees around a circumference of wires 23, the laser beam being approximately aligned with a longitudinal axis of filar ends 263. According to some embodiments of the present invention, a contour of the external surface of shroud 20 is such that filar ends 263 are lifted to form a gap g between ends 263 and the outer surface of shroud as illustrated in FIG. 2C;

although FIG. 2C illustrates a circular contour of the shroud outer surface, other contours facilitating formation of gap g, for example a more ovular contour or one including a flat surface underlying ends 263, are contemplated as embodiments of the present invention. According to other embodiments of the present invention, shroud 20 includes a protrusion 22 illustrated by dashed lines in FIGS. 2B–C, positioned in proximity to slot 2, to further lift ends 263 away from the outer surface of shroud 20. A minimum height of gap g may range from approximately 0.0005 inch to approximately 0.01 inch.

FIG. 2C further illustrates an alternate general direction of a laser beam L2 wherein energy of the beam may be reflected from the surface of shroud 20 back to filar ends 263. According to some embodiments of the present invention a surface finish of shroud 20 is such that sufficient laser energy is reflected to augment ablation of insulative layers 26 approximately 360 degrees about the circumference of ends 263. Such a surface finish may be textured or polished or a combination thereof to either focus or diffuse laser energy according to particular ablation requirements. It should be noted that the illustrated beams might vary from the general directions L1 and L2 depending upon a contour of the surface underlying ends 263 to take advantage of reflection. It should also be noted that, although the general directions L1 and L2 are illustrated with single arrow, multiple pulses of ablative energy of varying position and direction may be used to remove portions of insulation layers 26 from ends 263. Examples of appropriate ablative energy include that from $CO_2$ lasers or Excimer lasers; laser settings will vary depending on thickness and material composition of insulation layers 26. According to one example, in a set-up similar to that illustrated in FIG. 2B, with a feed rate setting of 0.005 and a pulse rate setting of 9, a $CO_2$ laser, directed per general direction L1, removed insulation layers 26 from ends 263, 360 degrees around; insulation layers were formed of ETFE having an approximate thickness of 0.002 inch, of polyimide having an approximate thickness of 0.0005 inch, or of composite polyimide and ETFE, the polyimide having a thickness of approximately 0.0005 inch and the ETFE, overlaying the polyimide, having a thickness of approximately 0.0015 inch.

According further embodiments of the present invention, the external surface of shroud 20 includes a recess 24 underlying ends 263, as illustrated with dashed lines in FIG. 2B; recess 24 may have a specialized contour and surface finish to further enhance reflected energy from either direction L1 or L2 or may simply enhance gap g between ends 263 and the external surface of shroud 20.

Figure 3:
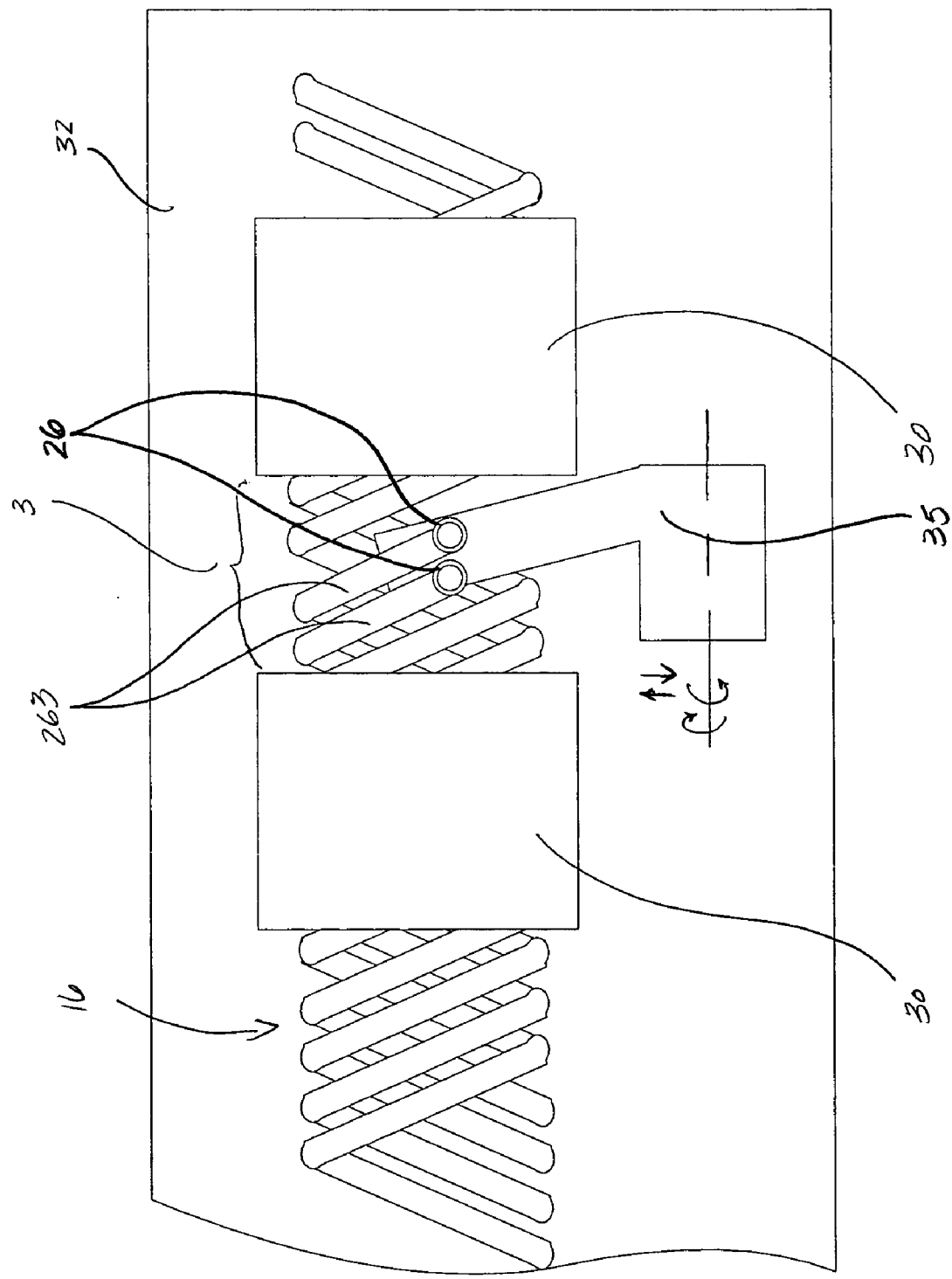
FIG. 3 is a plan view of a conductor coil and an alternate embodiment of a shroud and further illustrating steps according to a method of the present invention.

FIG. 3 is a plan view of a conductor coil and an alternate embodiment of a shroud 30, wherein coil 16 is positioned. FIG. 3 illustrates shroud 30 including two parts mounted on a fixture plate 32 and spaced apart to provide an opening 3 for removal of insulation layers 26 from ends 263; one or both of the two parts of shroud 30 may include a clamping mechanism or an adjustable inner surface to fixedly engage coil 16 on fixture 32 while transferring coil 16 into a predetermined position for the removal process and, according to some embodiments, during the removal process. FIG. 3 further illustrates a lever mechanism 35, which may or may not be coupled to fixture plate 32; according to the illustrated embodiment, lever mechanism 35 is adapted for translation and rotation, per the illustrated arrows, so that lever 35 may travel into opening 3 and rotate to lift filar ends 263, thus orienting filar ends 263 for ablation of insulation 26 as was previously described in conjunction with FIGS. 2B–C. According to an alternate embodiment, lever mechanism 35 is fixed in the illustrated position and coil 16 is rotated to elevate or lift filar ends 263 upon lever 35.

Figure 4:
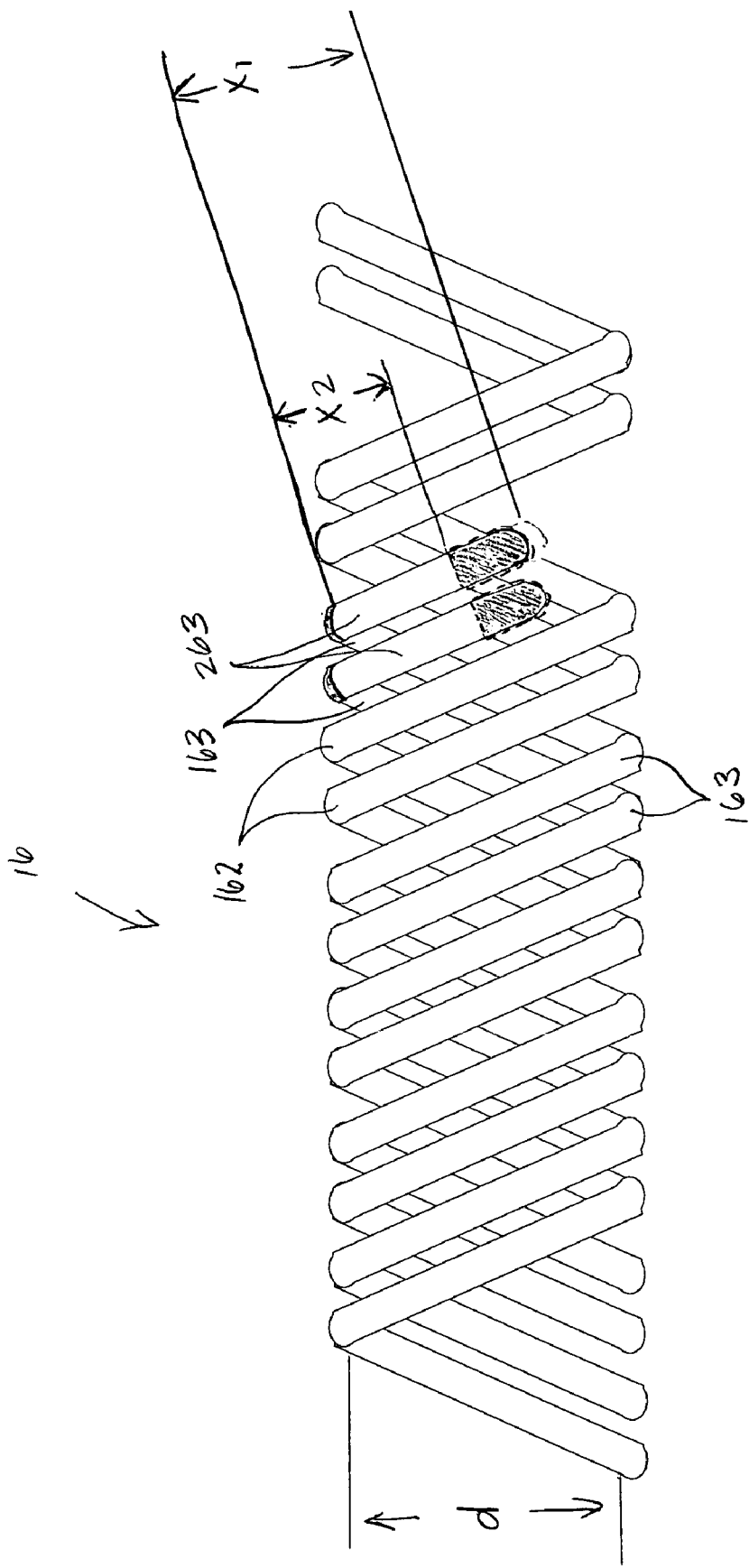
FIG. 4 is a plan view of a conductor coil according to one embodiment of the present invention.

FIG. 4 is a plan view of conductor coil 16 upon separation from a shroud fixture following the removal of insulation 26 from filar ends 263. FIG. 4 illustrates alternate lengths x1 and x2 along filar ends 263 from which the insulation has been removed. According to one embodiment insulation is removed to the very tip of filar ends 263 as illustrated by length x1; according to another embodiment some insulation is left at the very tip of filar ends 263 as illustrated by length x2. Lengths x1 and x2 may range from approximately 1 millimeter to approximately 5 millimeters.

Figure 5A:
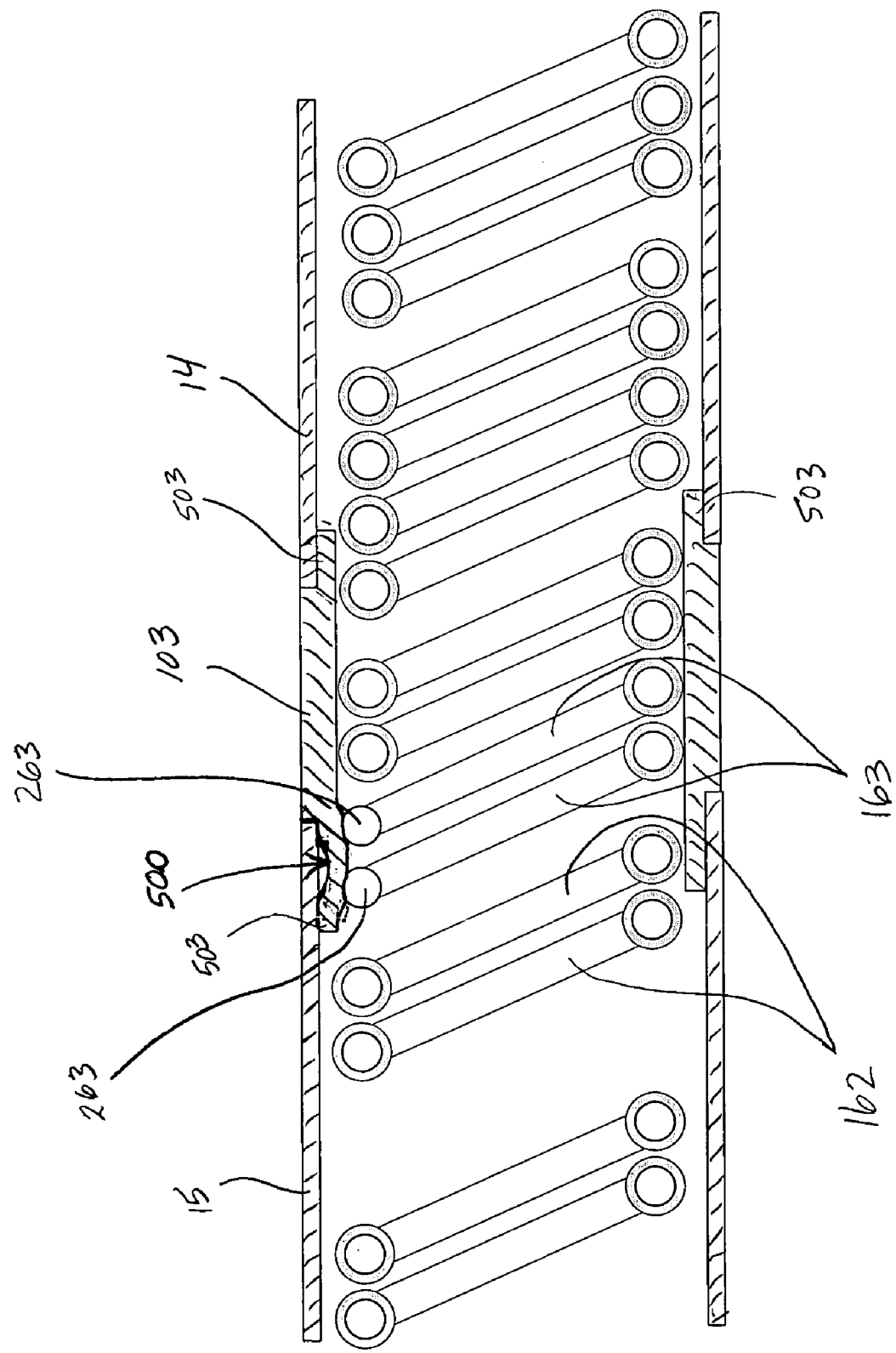
FIG. 5A is a section view through section line A—A of FIG. 1.

FIG. 4 further illustrates that, according to some embodiments, lifting of filar ends 263 for insulation removal by either of the previously described methods does not plastically deform filars 163 so that filars 163 may return to approximately a common inner diameter d of coil 16. Coil 16, as illustrated in FIG. 4 may now be assembled within a lead body, for example lead body 12 illustrated in FIG. 1, being coupled to an electrode, for example electrode 103, at filar ends 263, from which insulation has been removed. Such a coupling, is illustrated in FIG. 5A. It should be noted that opposite ends of filar pair 163 may also have insulation removed by one of the methods described herein for coupling to a connector contact, for example connector contact 108 shown in FIG. 1.

Figure 5B:
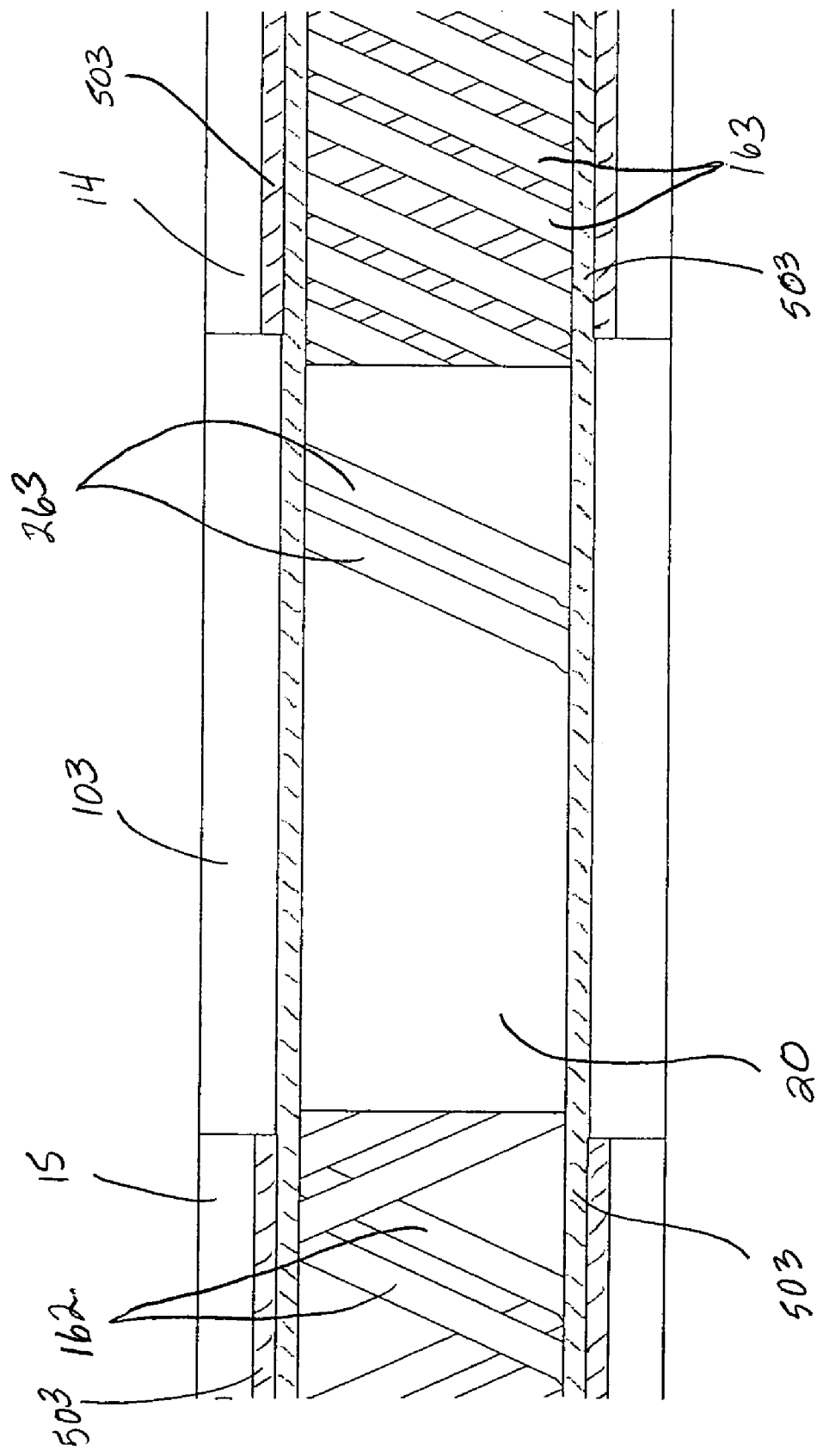
FIG. 5B is a section view through section line B—B of FIG. 1.

FIG. 5A is a section view through section line A—A of FIG. 1 according to one embodiment of the present invention. FIG. 5A illustrates filar ends 263 of coil 16 free of insulation and welded to an internal extension 503 of electrode 103 at a junction 500; any means known to those skilled in the art may be used to form weld junction 500. According to an alternate embodiment of the present invention, a shroud, for example shroud 20 illustrated in FIGS. 2A–C, doubles as a supporting component within a lead body assembly as is illustrated in FIG. 5B. FIG. 5B is a section view through line B—B of FIG. 1 according to this alternate embodiment wherein coil 16 is not separated from shroud 20 after insulation removal; rather, electrode 16 is coupled to filar ends 263, which remain supported on the outer surface of shroud 20, by a press fit or a crimp. Again, it should be noted that although FIGS. 5A–B illustrate sections through electrode portions of lead body 12, the structure illustrated could also be incorporated at the connector end of the lead body 12 as a coupling of coil 16 to connector contact 108.

Finally, it will be appreciated by those skilled in the art that while the invention has been described above in connection with particular embodiments and examples, the invention is not necessarily so limited; numerous other embodiments and uses are intended to be encompassed by the claims attached hereto.

What is claimed is:

1. A method for forming an electrically active surface for a medical electrical lead comprising the steps of:
    inserting a conductor coil into a shroud that includes an opening exposing a portion of the inserted coil to an exterior of the shroud; the coil including a plurality of insulated wire filars having been coaxially wound to a common diameter;
    lifting an end of at least one filar out through the opening so that the filar end is positioned outside the shroud; and
    removing a layer of insulation from about the end of the at least one filar by means of ablation by a laser.

2. The method of claim 1, wherein an end of another filar extends within the shroud past the opening when the coil is inserted within the shroud and the end of the at least one filar is lifted.

3. The method of claim 1, wherein the layer of insulation removed from the end of the at least one filar extends around approximately 360 degrees of the end.

4. The method of claim 1, wherein a length of the layer of insulation removed from the end of the at least one filar extends between remaining layers of insulation.

5. The method of claim 1, wherein a length of the layer of insulation removed from the end of the at least one filar is from approximately 1 millimeter to approximately 5 millimeters.

6. The method of claim 1, wherein a length of the lifted end of the at least one filar is from approximately 1 millimeter to approximately 5 millimeters.

7. The method of claim 1, wherein the lifting step is performed by rotating the coil.

8. The method of claim 1, wherein the shroud comprises a tube and the lifting step positions the filar end about an outer surface of the tube.

9. The method of claim 8, wherein a gap is present between the outer surface of the tube and the lifted end of the at least one filar prior to the removal step.

10. The method of claim 9, wherein a minimum height of the gap is from approximately 0.0005 inch to approximately 0.01 inch prior to the removal step.

11. The method of claim 8, wherein the outer surface of the tube includes a protrusion adjacent an edge of the opening such that the lifted end of the at least one filar is further lifted by the protrusion.

12. The method of claim 8, wherein a gap is present between the outer surface of the tube and the lifted end of the at least one filar and the outer surface has a surface finish enabling reflected energy of the laser to augment the removal of the layer of insulation.

13. The method of claim 8, wherein the outer surface of the tube includes a recess in proximity to an edge of the opening such that the lifted end of the at least one filar is positioned over the recess resulting in a gap between the outer surface and the end.

14. The method of claim 13, wherein a surface of the recess beneath the lifted end of the at least one filar has a surface finish enabling reflected energy of the laser to augment the removal of the layer of insulation.

15. The method of claim 8, further comprising the steps of:
positioning a component over the tube and the end of the at least one filar after the insulation removal step; and
electrically coupling the component to the filar end.

16. The method of claim 15, wherein the component comprises a medical electrical lead electrode.

17. The method of claim 15, wherein the component comprises a medical electrical lead connector.

18. The method of claim 1, further comprising the step of orienting the lifted filar end with respect to the laser, or visa versa, such that a beam of the laser is directed in approximate alignment with a longitudinal axis of the end of the at least one filar.

19. The method of claim 1, wherein the shroud is adapted to fixedly engage the coil to a fixture.

20. The method of claim 1, wherein the lifting step is performed by a lever mechanism inserted within the shroud opening.

21. The method of claim 1, wherein the lifting step does not significantly plastically deform the at least one filar and further comprising the step of separating the shroud from the coil such that the end of the at least one filar, having insulation removed, returns to approximately the common diameter.

22. The method of claim 21, further comprising the steps of:
placing a conductive element over the coil in proximity to the end of the at least one filar; and
electrically coupling the conductive element to the end of the at least one filar.

23. The method of claim 22, wherein the conductive element includes a medical electrical lead electrode.

24. The method of claim 22, wherein the conductive element includes a medical electrical lead connector.

* * * * *